United States Patent
Bock et al.

(10) Patent No.: US 12,370,129 B2
(45) Date of Patent: Jul. 29, 2025

(54) STORAGE-STABLE DENTAL ADHESIVE SET FOR USE WITH PEROXIDICALLY AND HYDROPEROXIDICALLY REDOX-INITIATED COMPOSITES

(71) Applicant: Ivoclar Vivadent AG, Schaan (LI)

(72) Inventors: Thorsten Bock, Feldkirch (AT); Thomas Köhler, Reichenau (DE); Michael Barbisch, Klaus (AT)

(73) Assignee: Ivoclar Vivadent AG, Schaan (LI)

( * ) Notice: Subject to any disclaimer, the term of this patent is extended or adjusted under 35 U.S.C. 154(b) by 505 days.

(21) Appl. No.: 17/701,034

(22) Filed: Mar. 22, 2022

(65) Prior Publication Data

US 2022/0313563 A1    Oct. 6, 2022

(30) Foreign Application Priority Data

Mar. 31, 2021  (EP) .................................... 21166451

(51) Int. Cl.
*A61K 6/30* (2020.01)
*A61K 6/62* (2020.01)
*A61K 6/84* (2020.01)
*A61K 6/884* (2020.01)

(52) U.S. Cl.
CPC ................. *A61K 6/30* (2020.01); *A61K 6/62* (2020.01); *A61K 6/84* (2020.01); *A61K 6/884* (2020.01)

(58) Field of Classification Search
CPC ...................................................... A61K 6/61
See application file for complete search history.

(56) References Cited

U.S. PATENT DOCUMENTS

| | | | |
|---|---|---|---|
| 6,288,138 B1 | 9/2001 | Yamamoto et al. | |
| 6,857,805 B2 | 2/2005 | Galehr et al. | |
| 10,709,522 B2 | 7/2020 | Loh et al. | |
| 2007/0040151 A1 | 2/2007 | Utterodt et al. | |
| 2009/0060627 A1 | 3/2009 | Stubbs | |
| 2019/0298619 A1* | 10/2019 | Thalacker | A61K 6/64 |
| 2021/0085570 A1 | 3/2021 | Thalacker et al. | |
| 2021/0169749 A1 | 6/2021 | Mitamura et al. | |

FOREIGN PATENT DOCUMENTS

| | | | | |
|---|---|---|---|---|
| DE | 19956705 A1 | 6/2001 | | |
| EP | 0006757 A2 | 1/1980 | | |
| EP | 1103230 A2 | 5/2001 | | |
| WO | WO-2019211724 A2 * | 11/2019 | | A61K 6/30 |

OTHER PUBLICATIONS

3M Scotchbond Universal Adhesive Safety Data Sheet; Sep. 18, 2015 (Year: 2015).*
3M RelyX Ultimate Safety Data Sheet; Apr. 5, 2018 (Year: 2018).*
"Vanadium", Wikipedia, https://en.wikipedia.org/wiki/Vanadium, retrieved on Sep. 13, 2024.

* cited by examiner

Primary Examiner — Michael F Pepitone
(74) Attorney, Agent, or Firm — Ann M. Knab; Thad McMurray

(57) ABSTRACT

Dental adhesive set which contains an adhesive and an applicator which is coated with a vanadium(IV) salt.

15 Claims, 2 Drawing Sheets

STORAGE-STABLE DENTAL ADHESIVE SET FOR USE WITH PEROXIDICALLY AND HYDROPEROXIDICALLY REDOX-INITIATED COMPOSITES

CROSS-REFERENCE TO RELATED APPLICATIONS

This application claims priority to European Patent Application No. 21166451.1 filed on Mar. 31, 2021, the disclosure of which is incorporated herein by reference in its entirety.

TECHNICAL FIELD

The present invention relates to dental adhesives which are suitable for use with peroxidically and hydroperoxidically redox-initiated composites and which have a high level of storage stability.

BACKGROUND

The adhesive cementation of methacrylate-based composite materials is widely used in direct and indirect restoration treatment. In this process, a methacrylate-based adhesion promoter ("adhesive") is first deposited on the dental hard tissue to be treated. There are various types of such adhesives, which differ primarily in the type of use as well as the number of components. Some adhesives require a pretreatment of the hard tooth tissue with phosphoric acid (Total Etch or Etch & Rinse methods), other adhesives have self-etching properties (Self Etch methods). Adhesives usually consist of mixtures of different methacrylates ("monomers") in solvents. The monomers can contain one or more methacrylate groups and further functional groups. Further functional groups are used to provide particular product properties, such as e.g. carboxylic acid or phosphoric acid ester groups for self-etching and for promoting adhesion to dental hard tissue. The adhesives can additionally contain processing aids (e.g. rheology additives), stabilizers (radical scavengers), as well as photoinitiators and optionally parts of redox initiator systems.

After the adhesive has been deposited, the solvent or solvents is or are removed by aeration with an airstream and the adhesive layer forming is usually polymerized by exposure to light. The composite containing filler and methacrylates is then deposited on the surface of the adhesive in further steps. During the curing of the composite, adhesive and composite copolymerize, and thus lead to the desired mechanically resilient bond.

In the case of direct restoration treatment, the composite acts as filling material ("filling composite"). It is applied to the cured adhesive layer directly into the cavity as a flowable or tampable paste and moulded such that the desired shaping is achieved. In indirect restoration treatment, the composite is used to cement prefabricated restoration materials made of ceramic, metal or prepolymerized composite, such as e.g. crowns, inlays, onlays or veneers ("luting composite"). The luting composite here bridges the volume between the adhesive surface and the restoration material.

The curing of filling or luting composites is effected either by photochemical radical formation or by redox-chemical radical formation not dependent on light. The light curing of both adhesive and composite is usual in direct restoration treatment as the materials used there are usually sufficiently translucent. In indirect restoration treatment, however, not very translucent materials, such as e.g. oxide ceramics, or totally opaque materials, such as e.g. metals, are also widely used. In such cases, it is not possible to introduce the amount of light necessary for a photochemical polymerization into the composite, which leads e.g. to a lack of or greatly reduced mechanical resilience. Luting composites that polymerize by redox chemistry are therefore preferably used for indirect restoration treatment.

The redox-initiated polymerization usually used in the case of luting composites is based on the redox systems peroxide/amine ("peroxidically initiated composite") or hydroperoxide/thiourea ("hydroperoxidically initiated composite"). Hydroperoxidically initiated composites often additionally contain a transition metal compound. Both redox systems are widely used, but are usually not identified by the manufacturers and also cannot be distinguished by a person skilled in the art without chemical analysis of the composite. A dentist thus cannot tell whether a luting composite polymerizes using a peroxidic or hydroperoxidic redox system. This is a problem because adhesive and composite must be matched to each other.

A further problem is that the redox initiators used in luting composites, in particular the peroxide/amine system, are pH-sensitive and are inhibited by self-etching, e.g. carboxylic or phosphoric acid, adhesives, which brings about a reduction in the bond strength between adhesive and composite. In order to prevent this inhibition of the initiators of the composite, it is usually recommended by the adhesive manufacturer to cure the adhesive with light before the luting composite is deposited. In this way, the mobility of the acid groups of the adhesive is reduced through the integration into the polymer matrix, and the copolymerization between adhesive and composite is promoted.

The precuring of the adhesives can, however, lead to fit inaccuracies in the case of indirect restoration treatment as the thickness of the adhesive layer or the accumulation of adhesive on the cavity floor ("pooling") are difficult for the user to control. Indirect restorations are prefabricated as accurately fitting as possible with the aid of casts or digital scans of the tooth to be restored. However, the precision of the prefabrication has the result that even small changes in the cavity geometry which are made after the cast has been made or after the scanning, such as the application of an adhesive layer, can cause the restoration to become jammed when inserted. The use of light-cured adhesives in indirect restoration treatment therefore represents a potential source of defects.

EP 0 006 757 A2 discloses two-component dental filling composites which contain a rod-shaped mixing tool and a paste-like component. The curing of the composites is triggered by a two-part initiator system made of peroxide and amine. One initiator component is dissolved in the paste; the other is applied to the mixing tool. For activation, the paste is stirred with the mixing tool.

EP 0 923 924 A2 and corresponding U.S. Pat. No. 6,288,138, which US patent is hereby incorporated by reference in its entirety, discloses a dental adhesive kit which contains a radically polymerizable monomer with acid groups, a photoinitiator and/or a peroxide, a water-soluble organic solvent, sulfinic or barbituric acid and water. The sulfinic or barbituric acid can be applied to an applicator.

WO 2015/181227 A1 and corresponding U.S. Ser. No. 10/709,522, which US patent is hereby incorporated by reference in its entirety, relates to micro-applicators which are at least partially coated with metal, metal-containing compounds or metal-organic compounds and optionally additionally with further additives. The metal is preferably selected from iron, cobalt, nickel, ruthenium, rhodium, palladium, osmium, iridium, platinum, silver, copper, tin and zinc. Barbituric acid, sulfinic acids, carboxylic acids and amine salts among others are named as further additives. When these applicators are used to apply dental adhesives, improved adhesion values compared with uncoated applicators are said to be achieved.

DE 199 56 705 A1 discloses brush-shaped applicators for dental uses which are coated with a catalyst, e.g. with benzenesulfinic acid, and optionally with an amine such as diethanol-p-toluidine. For use, the applicators are dipped e.g. in a dental adhesive and the adhesive is then applied to the tooth with the applicator. In the process, the catalyst and the amine dissolve in the adhesive and bring about the curing. As catalyst and amine are present in dry form, the applicators are said to be particularly stable. With this system, optimum results are only achieved with peroxide-containing composites, but not with hydroperoxide-containing composites, which continue to prevail because of their much better storability.

One-component dental adhesives which contain an ionic transition metal compound are known from WO 2019/211724 A2 and corresponding US 20210085570, which US patent application is hereby incorporated by reference in its entirety. The adhesives are said to be suitable for use with composites which contain peroxides, peroxyesters, diacyl peroxides or persulfates as oxidants. Although these compositions contain stabilizers for improving the storage stability, their stability is insufficient for commercial purposes.

SUMMARY

The object of the invention is to provide an adhesive which is suitable for dental purposes and which does not have the above-described shortcomings. In particular, the adhesive is to be storage-stable and to offer a high degree of application safety. The adhesive is to be suitable for use with peroxidically and hydroperoxidically redox-initiated composites as well as for direct and indirect restorations.

BRIEF DESCRIPTION OF THE DRAWINGS

Further advantages, details and features will arise from the following description of an example embodiment of the invention while making reference to the drawings, wherein.

DETAILED DESCRIPTION

Figure 1:
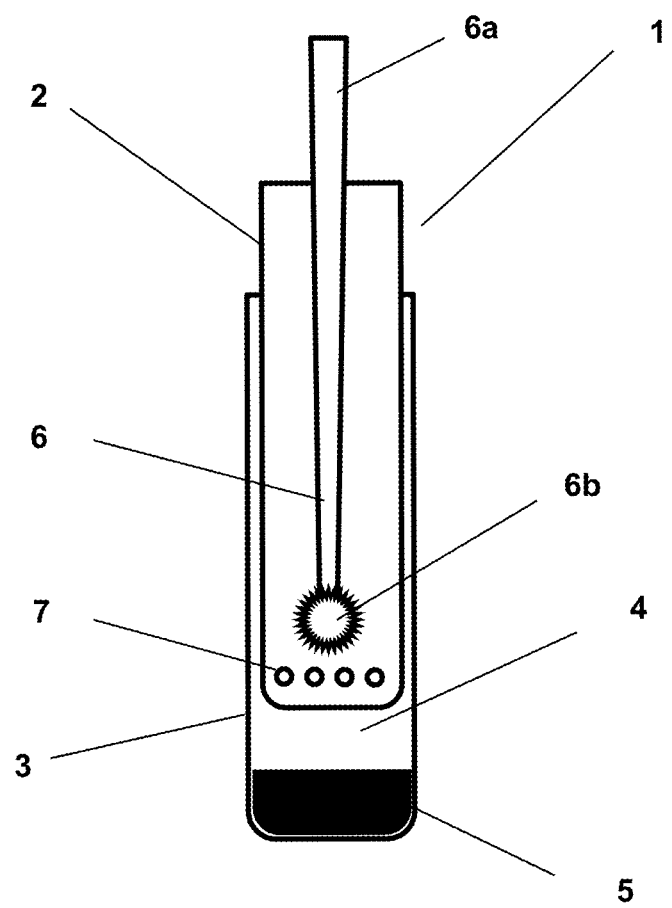
FIG. 1 shows a container in accordance with the invention.

According to the invention, the objects are achieved by a dental adhesive set which contains an adhesive and an applicator. The dental adhesive set is characterized in that the applicator is coated with at least one vanadium(IV) salt.

Applicator and adhesive are spatially separated from each other before use. For use, the adhesive is brought into contact with the coated applicator. The vanadium salt dissolves out of the coating and is mixed with the adhesive. The adhesive is then deposited on the tooth surface with the applicator, and then a hydroperoxide- or peroxide-containing composite is applied to the dried adhesive layer. After the composite has been applied, the hydroperoxide or the peroxide diffuses out of the composite into the adhesive and there forms free radicals, which start the radical polymerization, by reaction with the vanadium salt.

Vanadium(IV) salts preferred according to the invention are vanadyl acetylacetonate, vanadyl oxalate, vanadyl maltolate and vanadyl picolinate; vanadyl acetylacetonate, vanadyl oxalate and vanadyl picolinate are particularly preferred, and vanadyl oxalate is quite particularly preferred. These salts bring about an effective decomposition of peroxides and in particular of hydroperoxides, and thus result in a particularly firm bond between the adhesives and composites according to the invention. The vanadium(IV) salts are characterized, in comparison with Cu(II) salts, in that they are also active under acidic conditions, i.e. for example in the presence of acidic monomers.

The vanadium(IV) compounds are oxidized to vanadium (V) during the reaction with peroxides and hydroperoxides. The applicator therefore preferably also contains a reducing agent. The vanadium(V) formed is reduced to vanadium(IV) again by the reducing agent, and is thus available for the further reaction. The reducing agent moreover effectively prevents a deactivation of the vanadium(IV) salts by reaction with atmospheric oxygen, for example during production of the applicator. Ascorbic acid is a preferred reducing agent. Vanadyl picolinate and ascorbic acid, as well as vanadyl oxalate and ascorbic acid, are preferred combinations of vanadium salt and reducing agent. Because of the reducing properties of its anion, the vanadyl(IV) oxalate particularly preferred as vanadium(IV) salt according to the invention can also be used without an additional reducing agent.

In addition to ascorbic acid itself, derivatives of ascorbic acid can advantageously also be used. Preferred derivatives are salts, esters and ethers of ascorbic acid. Preferred salts are the alkali and alkaline earth metal salts such as sodium ascorbate and magnesium ascorbate. Preferred esters are $C_8$-$C_{18}$ fatty acid esters, in particular palmitoyl ascorbate. Preferred ethers are $C_1$-$C_4$ alkyl ethers, particularly preferably 3-O—$C_1$-$C_4$ alkyl ethers, quite particularly preferably 3-O-ethyl ascorbic acid.

The reducing agent can be present in the same layer as the vanadium(IV) salt or in a separate layer. According to the invention, it is preferred that the reducing agent and the vanadium(IV) salt are located in the same layer.

The applicator according to the invention is preferably additionally coated with a sulfinic acid and/or a sulfinic acid derivative. Sulfinic acids and sulfinic acid derivatives, together with peroxides, form free radicals, and the additional coating of the applicators with at least one sulfinic acid or sulfinic acid derivative therefore improves in particular the bond of the adhesives according to the invention with peroxidically initiated composites. Preferred sulfinic acids are benzenesulfinic acid and 4-methylbenzenesulfinic acid. Preferred sulfinic acid derivatives are sulfinic acid esters and particularly sulfinic acid salts. Particularly preferred salts are the alkali metal salts; the alkali metal salts of benzenesulfinic acid and of 4-methylbenzenesulfinic acid, in particular sodium benzenesulfinate or lithium benzenesulfinate, are quite particularly preferred. Vanadyl(IV) oxalate is characterized in that it achieves high adhesion values both with peroxide-containing composites and with hydroperoxide-containing composites, even without sulfinic acid or sulfinic acid derivative. According to an embodiment of the invention, applicators which are coated with vanadyl(IV) oxalate and which contain no reducing agent, no sulfinic acid and no sulfinic acid derivative are therefore particularly preferred.

For the sake of simplicity, reference is usually only made to ascorbic acid or sulfinic acid in the following. However, in both cases, unless otherwise indicated, the respective esters, salts and derivatives are also meant.

In addition to the named substances, the coating of the applicators according to the invention can contain further additives, in particular one or more rheology additives. Rheology additives are divided into thixotropic agents and thickeners. Fumed and precipitated silicas are particularly suitable as thixotropic agents. Silicas with a primary particle diameter of from 5 to 500 nm are particularly preferred. Silicas with spherical particles are particularly preferred. Polymers, in particular polyacrylic acid, polyitaconic acid, polyvinyl alcohol, polystyrene and derivatives and copolymers thereof, are preferred as thickeners. By derivatives of the polymers in question is meant here derivatives of the respective polymers modified by bonding of ester or ether groups. Methacrylate-modified polyacrylic and polyitaconic acids are of particular interest within the meaning according to the invention. The polymers used here preferably have a weight-average molar mass of from 5,000 to 100,000 g/mol. The molar mass of the polymers is preferably determined by means of vapour pressure osmometry, ebullioscopy or cryoscopy.

The coating of the applicators according to the invention preferably contains no amines, in particular no N,N-dialkyl arylamines, such as e.g. Chivacure EPD, N,N-dimethyl-ethyl-p-aminobenzoate or DABA, N,N-diethylamine-3,5-di-tert-butylaniline, or aliphatic amines, such as e.g. dimethylaminoethyl methacrylate, DMAEMA, since it has been found that amines can impair the enamel adhesion of the adhesives.

The microbrushes widely used for adhesive application, i.e. small brushes in which one end of a rod-shaped brush shaft is provided with a coating (flocking, sponge, bristles, rubber lamellae, etc.) that is suitable for depositing liquids, are particularly suitable as applicators. Suitable applicators are described for example in DE 199 56 705 A1. Syringe cannulas or snap-on cannulas, in which a suitable metal or plastic tube is provided with a coating (flocking, sponge, bristles, rubber lamellae, etc.) suitable for depositing liquids at one end and has a receiver (e.g. Luer lock) compatible with a liquid container, e.g. a syringe, at the other end, can likewise be used. The applicator can be connected to a liquid container which is used to hold the adhesive, such as e.g. a pen applicator.

It has surprisingly been found that the coating sequence during the application of the layers to the applicator has a decisive influence on the later adhesion between adhesive and composite. According to the invention, the applicator is preferably first coated with a vanadium(IV) salt or a mixture of vanadium(IV) salts, wherein this first layer preferably also contains a reducing agent. Only after that is the applicator coated with a sulfinic acid or a mixture of sulfinic acids, with the result that a second (outer) layer is formed. Applicators coated in the described manner result in much better adhesion values with peroxidically initiated composites than applicators in which sulfinic acid(s) and vanadium (IV) salt(s) were applied to the applicator in the reverse sequence or at the same time.

A method for producing coated applicators and the applicators obtained are also subjects of the invention. According to the invention, the coating of the applicators is preferably effected in a dipping process, which comprises the following steps:

(1) providing a solution of one or more vanadium(IV) salts in a suitable solvent,
(2) dipping an applicator into the solution from step (1) one or more times, preferably for at least 5 seconds, preferably 10 to 60 seconds, in each case,
(3) drying the applicator from step (2), preferably at a temperature of 70° C. and preferably for a maximum of 15 minutes, and preferably
(4) providing a solution of one or more sulfinic acids and/or sulfinic acid derivatives in a suitable solvent,
(5) dipping the applicator into the solution from step (4) one or more times, preferably for at least 5 seconds, preferably 10 to 60 seconds, in each case, and
(6) drying the applicator from step (5), preferably at a temperature of 70° C., preferably for a maximum of 15 minutes.

In addition to the vanadium(IV) salt or salts, the solution used in step (1) preferably also contains a reducing agent, particularly preferably ascorbic acid. To increase the loading of the applicator, the dipping steps can in each case be carried out one or more times. Should the applicator be dipped into the solution from step (1) or step (4) multiple times in step (2) and/or in step (5), it is preferably dried after each dip, preferably under the above-named conditions. A layer formed by multiple dipping into the same solution and optionally subsequent drying is regarded as one (1) layer according to the invention. The layer is formed by several plies in this case.

Should the applicator be coated with more than one sulfinic acid and/or more than one sulfinic acid derivative, step (4) can be split into several separate steps, in that the applicator is first dipped into a solution with a first sulfinic acid or a first sulfinic acid derivative and then into a further solution with a second sulfinic acid or a second sulfinic acid derivative. In the case of more than two sulfinic acids or sulfinic acid derivatives, the number of solutions can be correspondingly adapted. Here too, the applicator is preferably dried before being dipped into a further solution. The same applies analogously when the applicator is coated with more than one vanadium salt. If the applicator is only to be coated with one or more vanadium(IV) salts, steps (4) to (6) can be omitted.

To avoid repeated dipping steps, the viscosity of the coating solutions can be increased by adding rheology additives, with the result that a larger quantity of the solution remains adhering to the applicator during dipping.

The applicator is preferably only partially dipped into the solution from step (1) in steps (2) and (5), with the result that only part of the applicator is coated and the rest remains uncoated. The uncoated part of the applicator can be used e.g. as a handle for holding the applicator. However, it is also possible to completely coat the applicator and connect it to a suitable handle later.

The concentrations of the solutions and optionally the number of dipping steps are chosen so that such quantities of the components are deposited on the applicator as are suitable for curing the quantity of the adhesive to be applied.

A preferred solvent for producing the vanadium(IV) salt solution in step (1) is methanol, because a concentration of vanadium salt advantageous for the coating can be achieved herein. Moreover, the solvent is easy to remove after the coating. The reducing agents, such as e.g. ascorbic acid, optionally used to stabilize the vanadium(IV) salt are also very soluble in methanol. The vanadium(IV) salt concentration is preferably 0.5 to 5 wt.-%, particularly preferably 1 to 2 wt.-%. The concentration of the reducing agent is preferably 0.5 to 5 wt.-%, particularly preferably approx. 1 wt.-%. Solutions which contain approx. 2 wt.-% vanadyl picolinate and approx. 1 wt.-% ascorbic acid or 1 wt.-% vanadyl oxalate are quite particularly preferred.

Unless otherwise indicated, all wt.-% and ppm given herein refer to the total mass of the respective composition.

To produce the sulfinic acid solution in step (4), ethanol is preferred as solvent. Ethanol has the advantage that sulfinic acids and sulfinic acid salts such as sodium benzenesulfinate are very soluble in it, but vanadium salts and reducing agents are only relatively poorly soluble therein, with the result that the previously applied layer of vanadium salt and reducing agent is not detached again, or not to a functionally relevant extent. The sulfinic acid or sulfinic acid salt concentration is preferably 1 to 10 wt.-%, particularly preferably approx. 2 wt.-%. A solution which contains approx. 2 wt.-% sodium benzenesulfinate is quite particularly preferred.

In general, the solvents for producing the coating solutions are chosen such that the layer applied in one method step is not detached again in the subsequent step. As the solubility of different sulfinic acids or vanadium salts can vary, it may be necessary to adapt the choice of the solvents accordingly.

The drying in steps (3) and (6) is preferably effected in each case in a temperature range of from room temperature (20° C.) to 70° C., particularly preferably at 40° C. to 70° C., quite particularly preferably at approx. 40° C. The drying time is preferably 5 to 10 minutes. The drying can be effected e.g. in a drying cabinet. The drying has the effect that the components remain adhering to the applicator.

Through the above sequence of steps, a high level of storage stability and an optimum adhesion to the tooth are achieved, both when the adhesive is used with peroxidically initiated composites and when it is used with hydroperoxidically initiated composites.

A particular advantage of the applicators according to the invention is that the layers can be applied directly one after the other in the described manner, without the use of a separating layer between the vanadium salt layer and the sulfinic acid or sulfinic acid derivative layer being necessary. According to a preferred embodiment, the applicators therefore have only one vanadium salt layer and optionally one sulfinic acid or sulfinic acid derivative layer.

Vanadyl(IV) salts are preferably applied to the applicator in a quantity of from 30 to 100 µg, particularly preferably 40 to 90 µg and quite particularly preferably 50 to 80 µg. All specifications relate to the quantity per applicator. According to the invention, microbrushes which are coated on average with 50 to 80 µg vanadyl(IV) oxalate and snap-on cannulas which are coated on average with approx. 50 µg vanadyl(IV) oxalate are particularly preferred.

Sulfinic acid and sulfinic acid derivatives are preferably applied in a quantity of from 60 to 200 µg, particularly preferably 80 to 180 µg and quite particularly preferably 100 to 160 µg per applicator.

Reducing agents such as ascorbic acid and ascorbic acid derivatives are preferably applied in a quantity of from 15 to 50 µg, particularly preferably 20 to 45 µg and quite particularly preferably 25 to 40 µg per applicator.

The adhesive according to the invention preferably contains
  (a) at least one radically polymerizable acidic monomer,
  (b) at least one radically polymerizable monomer without acidic groups,
  (c) at least one water-miscible organic solvent and
  (d) water.
  Moreover, the adhesive preferably also contains
  (e) one or more thixotropic agents and/or fillers and/or
  (f) one or more stabilizers.
  Furthermore, the adhesive can contain one or more initiators for the photochemically triggered radical polymerization (photoinitiator) as component (g) and/or a thickener as component (h). The adhesive preferably contains no transition metal compounds and in particular no vanadium (IV) salts.

The adhesive according to the invention preferably contains one or more acid-group-containing radically polymerizable monomers (adhesive monomers; acidic monomers) as constituent (a). Acidic monomers which have at least one carboxylic acid group, sulfonic acid group, phosphonic acid group, phosphoric acid ester group, preferably a monohydrogen phosphate group or dihydrogen phosphate group as acid groups are preferred. Acidic monomers with dihydrogen phosphoric acid ester groups are quite particularly preferred.

Preferred monomers with carboxylic acid groups are maleic acid, acrylic acid, methacrylic acid, 2-(hydroxymethyl)acrylic acid, 4-(meth)acryloyloxyethyltrimellitic acid, 10-methacryloyloxydecylmalonic acid, N-(2-hydroxy-3-methacryloyloxypropyl)-N-phenylglycine or 4-vinylbenzoic acid.

Preferred monomers with phosphonic acid groups are vinylphosphonic acid, 4-vinylphenylphosphonic acid, 4-vinylbenzylphosphonic acid, 2-methacryloyloxyethylphosphonic acid, 2-methacrylamidoethylphosphonic acid, 4-methacrylamido-4-methyl-pentylphosphonic acid, 2-[4-(dihydroxyphosphoryl)-2-oxa-butyl]-acrylic acid or 2-[4-(dihydroxyphosphoryl)-2-oxa-butyl]-acrylic acid ethyl- and -2,4,6-trimethylphenyl ester as well as ß-ketophosphonic acid methacrylates, such as e.g. 9-methacryloyloxy-2-oxononylphosphonic acid. The ß-ketophosphonic acid methacrylates described in WO 2014/202176 A1 are particularly preferred.

Preferred monomers with phosphoric acid ester groups are 2-methacryloyloxypropyl mono- or dihydrogen phosphate, 2-methacryloyloxyethyl mono- or dihydrogen phosphate, 2-methacryloyloxyethylphenyl hydrogen phosphate, dipentaerythritolpentamethacryloyloxy phosphate, 10-methacryloyloxydecyl dihydrogen phosphate, phosphoric acid mono-(1-acryloyl-piperidin-4-yl) ester, 6-(methacrylamido) hexyl dihydrogen phosphate and 1,3-bis-(N-acryloyl-N-propylamino)-propan-2-yl di hydrogen phosphate.

Preferred monomers with sulfonic acid groups are vinylsulfonic acid, 4-vinylphenylsulfonic acid or 3-(methacrylamido)propylsulfonic acid.

Particularly preferred acidic monomers are 4-(meth)acryloyloxyethyltrimellitic acid anhydride, 10-methacryloyloxydecylmalonic acid, 2-methacryloyloxyethylphosphonic acid, 2-methacrylamidoethylphosphonic acid, 2-[4-(dihydroxyphosphoryl)-2-oxa-butyl]-acrylic acid, 2-[4-(dihydroxyphosphoryl)-2-oxa-butyl]-acrylic acid ethyl or -2,4,6-trimethylphenyl ester. 2-Methacryloyloxypropyl mono- or dihydrogen phosphate, 2-methacryloyloxyethyl mono- or dihydrogen phosphate, 2-methacryloyloxyethylphenyl hydrogen phosphate, 6-(methacrylamido)hexyl dihydrogen phosphate, 1,3-bis-(N-acryloyl-N-propyl-amino)-propan-2-yl dihydrogen phosphate and in particular 10-methacryloyloxydecyl dihydrogen phosphate.

The adhesive preferably contains a non-acidic radically polymerizable monomer or mixtures of radically polymerizable monomers as constituent (b). (Meth)acrylates are preferred, mixtures of mono- and polyfunctional (meth)acrylates are particularly preferred, and mixtures of mono- and difunctional (meth)acrylates are quite particularly preferred. By mono(meth)acrylates is meant compounds with one, by di- and polyfunctional (meth)acrylates is meant compounds with two or more, preferably 2 to 4, radically polymerizable groups. Methacrylates are preferred over acrylates in all cases.

Preferred mono- or polyfunctional (meth)acrylates are methyl, ethyl, 2-hydroxyethyl, 2-hydroxypropyl, n-butyl, benzyl, tetrahydrofurfuryl or isobornyl (meth)acrylate, 2-acetoacetoxyethyl methacrylate, p-cumyl-phenoxyethylene glycol methacrylate (CMP-1E), bis-GMA (an addition product of methacrylic acid and bisphenol A diglycidyl ether), UDMA (an addition product of 2-hydroxyethyl methacrylate (HEMA) and 2,2,4-trimethyl-hexamethylene diisocyanate), tricyclic UDMA (V-818; CAS No. 1998085-44-1) or the isomeric mixture thereof (CAS No. 106981-29-7), larly preferred mixtures of mono- and difunctional (meth) acrylates are mixtures of HEMA with bis-GMA and 1,10-decanediol dimethacrylate or of HEMA, V-818 and 1,10-decanediol dimethacrylate. Adhesives which contain 18 to 25 wt.-% HEMA, 18 to 25 wt.-% V-818 and/or bis-GMA and 6 to 10 wt.-% 1,10-decanediol dimethacrylate, in each case relative to the total mass of the adhesive, are quite particularly preferred.

The adhesive according to the invention contains a water-miscible organic solvent, preferably ethanol, methanol,

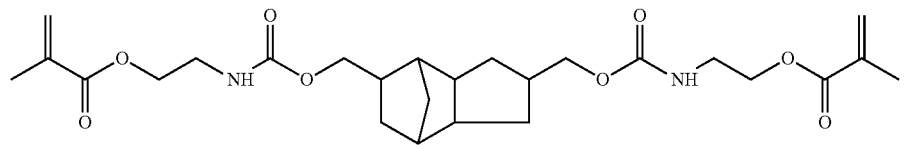 [SMILES: C=C(C)C(=O)OCCNC(=O)OCC1CC2C3CC(COC(=O)NCCOC(=O)C(=C)C)C(C3)C2C1]

2-propenoic acid, 2-methyl, 1,1'-[(octahydro-4,7-methano-1H-indene-2,5-diyl) bis(methyleneoxycarbonylimino-2,1-ethanediyl)] ester (CAS No. 1998085-44-1), TMX-UDMA (an addition product of a mixture of HEMA and hydroxypropyl methacrylate (HPMA) with α,α,α',α'-tetramethyl-m-xylylene diisocyanate (TMXDI)), bis(methacryloyloxymethyl)tricyclo[5.2.1.]decane (TCDMA), ethoxylated or propoxylated bisphenol A di(meth)acrylate, such as e.g. the bisphenol A dimethacrylate 2-[4-(3-methacryloyloxyethoxyethyl)phenyl]-2-[4-(3-methacryloyloxyethyl)phenyl]propane) (SR-348C) with 3 ethoxy groups or 2,2-bis[4-(2-(meth)acryloxypropoxy)phenyl]propane, di-, tri- or tetraethylene glycol di(meth)acrylate, trimethylolpropane tri(meth)acrylate, pentaerythritol tetra(meth)acrylate, as well as glycerol di(meth)acrylate acetate, glycerol di(meth)acrylate, 1,4-butanediol di(meth)acrylate, 1,10-decanediol di(meth)acrylate or 1,12-dodecanediol di(meth)acrylate, glycerol trimethacrylate (GTMA) and mixtures thereof.

N-mono- or N-disubstituted acrylamides, such as e.g. N-ethylacrylamide, N,N-dimethylacrylamide, N-(2-hydroxyethyl)acrylamide or N-methyl-N-(2-hydroxyethyl) acrylamide, or N-monosubstituted methacrylamides, such as e.g. N-ethylmethacrylamide or N-(2-hydroxyethyl)ethacrylamide as well as N-vinylpyrrolidone or allyl ether are further preferred. These monomers are characterized by a low viscosity and a high hydrolytic stability and are particularly suitable as diluting monomers.

Crosslinking pyrrolidones, such as e.g. 1,6-bis(3-vinyl-2-pyrrolidonyl)-hexane or commercially available bisacrylamides, such as methylene- or ethylenebisacrylamide, or bis(meth)acrylamides, such as e.g. N,N'-diethyl-1,3-bis(acrylamido)-propane, 1,3-bis(methacrylamido)-propane, 1,4-bis(acrylamido)-butane or 1,4-bis(acryloyl)-piperazine, which can be synthesized by reaction from the corresponding diamines with (meth)acrylic acid chloride, are likewise preferred. These monomers are characterized by a high hydrolytic stability and are particularly suitable as crosslinking monomers.

Particularly preferred monomers are HEMA, CMP-1E, bis-GMA, tricyclic UDMA (V-818; CAS No. 1998085-44-1 or 106981-29-7), UDMA, TMX-UDMA, TCDMA, ethoxylated or propoxylated bisphenol A dimethacrylate, SR-348c, triethylene glycol dimethacrylate, glycerol dimethacrylate, 1,10-decanediol dimethacrylate (D3MA), glycerol trimethacrylate (GTMA), N,N'-diethyl-1,3-bis(acrylamido) propane, maleic acid anhydride and mixtures thereof. Particun-propanol, isopropyl alcohol, acetone and methyl ethyl ketone or a mixture thereof, as constituent (c).

Constituent (d) is water, preferably distilled or deionized water. The water is free of impurities and is preferably sterile.

Furthermore, the adhesive can preferably also contain one or more thixotropic agents and/or fillers as constituent (e). Adhesives which contain at least one organic or particularly preferably inorganic particulate filler or a mixture thereof are preferred. The filler addition is preferably made to improve the mechanical properties, to adapt the viscosity and to optimize the rheological properties. Amorphous spherical materials are preferred as fillers, based on oxides, in particular $SiO_2$, such as e.g. fumed silica or precipitated silica (weight-average particle size of 10-1,000 nm) as well as minifillers, such as quartz, glass ceramic or X-ray-opaque glass powders of e.g. barium or strontium aluminium silicate glasses (weight-average particle size of 0.01-10 μm, particularly preferably 0.01-1 μm, quite particularly preferably 0.2-1 μm). Further preferred fillers are X-ray-opaque fillers, such as ytterbium trifluoride or nanoparticulate tantalum(V) oxide or barium sulfate or mixed oxides of $SiO_2$ with ytterbium(III) oxide or tantalum(V) oxide (weight-average particle size of 10-1,000 nm). The dental materials according to the invention preferably contain no ion-releasing fillers, in particular no $Ca^{2+}$- or $Al^{3+}$-releasing glasses.

Unless otherwise indicated, all particle sizes are weight-average particle sizes (D50 values), wherein the particle size determination in the range of from 0.1 μm to 1,000 μm is preferably effected by means of static light scattering, for example using an LA-960 Static Laser Scattering Particle Size Distribution Analyzer (Horiba, Japan). Here, a laser diode with a wavelength of 655 nm and an LED with a wavelength of 405 nm are used as light sources. The use of two light sources with different wavelengths makes it possible to measure the entire particle-size distribution of a sample in only one measurement pass, wherein the measurement is carried out as a wet measurement. For this purpose, a 0.1 to 0.5% aqueous dispersion of the filler is prepared and the scattered light thereof is measured in a flow cell. The scattered light analysis for calculating particle size and particle-size distribution is effected in accordance with the Mie theory according to DIN/ISO 13320. The measurement of the particle size in the range of from 5 nm to 0.1 μm is preferably effected by dynamic light scattering (DLS) from aqueous particle dispersions, preferably using an He—Ne laser with a wavelength of 633 nm, at a scattering angle of 90° and at 25° C., e.g. using a Malvern Zetasizer Nano ZS (Malvern Instruments, Malvern UK).

Particle sizes smaller than 0.1 μm can also be determined by means of SEM or TEM micrographs. The transmission electron microscopy (TEM) is preferably carried out using a Philips CM30 TEM at an accelerating voltage of 300 kV. For the sample preparation, drops of the particle dispersion are applied to a 50 Å thick copper grid (mesh size 300 mesh), which is coated with carbon, and then the solvent is evaporated. The particles are counted and the arithmetic mean is calculated.

To improve the bond between the filler particles and the crosslinked polymerization matrix, $SiO_2$-based fillers can be surface-modified with methacrylate-functionalized silanes, such as e.g. 3-methacryloyloxypropyltrimethoxysilane.

The adhesive preferably contains one or more stabilizers as component (f). These are radical-scavenging substances for preventing a premature polyreaction. The stabilizers are also called polymerization inhibitors. The inhibitors or stabilizers improve the storage stability of the materials.

Preferred inhibitors are phenols, such as hydroquinone monomethyl ether (MEHQ) or 2,6-di-tert-butyl-4-methylphenol (BHT). Phenols are preferably used in a concentration of from 0.001 to 0.50 wt.-%. Further preferred inhibitors are phenothiazine, the 2,2-diphenyl-1-picrylhydrazyl (DPPH) radical, the galvinoxyl radical, the triphenylmethyl radical and the 2,2,6,6-tetramethylpiperidine 1-oxyl (TEMPO) radical. These inhibitors are preferably used in a quantity of from 0.001 to 0.02 wt.-%. A polymerization does not take place until these additives are used up. The quantities relate in each case to the total mass of the material. A mixture of inhibitors which contains at least one phenol and at least one of the further initiators is preferably used.

The curing of the adhesives according to the invention is effected by an interaction of adhesive, applicator and composite. For use, the adhesive is brought into contact with the coated applicator. The vanadium salt and optionally the sulfinic acid dissolve out of the coating and are mixed with the adhesive. Then, the latter is applied to the enamel or dentine surface and dried by removal of the solvent. After that, a hydroperoxide- or peroxide-containing composite is applied to the dried adhesive layer. After the composite has been applied, hydroperoxide or peroxide diffuses out of the composite into the adhesive and triggers the polymerization there.

In order to make an additional light curing possible when necessary, the adhesive can contain a photoinitiator for the radical polymerization as constituent (g). Preferred photoinitiators are benzophenone, benzoin and derivatives thereof or α-diketones or derivatives thereof, such as 9,10-phenanthrenequinone, 1-phenyl-propane-1,2-dione, diacetyl or 4,4'-dichlorobenzil. Particularly preferred initiators are camphorquinone and 2,2-dimethoxy-2-phenyl-acetophenone and quite particularly preferably α-diketones in combination with amines as reducing agent, such as e.g. 4-(dimethylamino)benzoic acid ethyl ester, N,N-dimethylaminoethyl methacrylate, N,N-dimethyl-sym.-xylidine or triethanolamine. Norrish type I photoinitiators, above all acyl- or bisacylphosphine oxides, monoacyltrialkyl- or diacyldialkylgermanium compounds, such as e.g. benzoyltrimethylgermanium, dibenzoyldiethylgermanium or bis(4-methoxybenzoyl)diethylgermanium, are also particularly preferred. Advantageously, mixtures of the different photoinitiators can also be used, such as e.g. dibenzoyldiethylgermanium in combination with camphorquinone and 4-dimethylaminobenzoic acid ethyl ester. Photoinitiators are added in particular for when adhesive is used in direct filling treatment.

Adhesives which contain at least one thickener (h) as rheology additive are further preferred, wherein the above-named thickeners are preferred, i.e. in particular polyacrylic acid, polyitaconic acid, polyvinyl alcohol, polystyrene and/or derivatives or copolymers thereof. Methacrylate-modified polyacrylic and polyitaconic acid, e.g. polyacrylic acid modified with glycidyl methacrylate or methacrylic acid 2-isocyanatoethyl ester, are particularly preferred. Polymers with a weight-average molar mass of from 5,000 to 100,000 g/mol, in particular 5,000 to 50,000 g/mol, are quite particularly preferred. It was found that, in addition to their actual function, the thickeners preferred according to the invention improve the adhesion of the adhesives to dental hard tissue. Thickeners are preferably used in a quantity of from 0.1 to 8 wt.-%, particularly preferably 0.2 to 7 wt.-% and quite particularly preferably 3 to 6 wt.-%.

Adhesives which additionally contain at least one alkali metal hydroxide, preferably NaOH, KOH and/or RbOH, particularly preferably KOH and/or RbOH and quite particularly preferably KOH, are preferred according to the invention. The alkali metal hydroxide or hydroxides are preferably used in a total quantity of from 3 to 15 mmol, preferably 6 to 12 mmol per 100 g adhesive.

Optionally, the compositions according to the invention can moreover contain further additives, for example flavouring agents, colorants, microbiocidal active ingredients, fluoride-ion-releasing additives, optical brighteners, fluorescent agents, plasticizers, chain transfer reagents and/or UV absorbers.

According to the invention, the adhesive preferably has the following composition:
- (a) 1 to 40 wt.-%, preferably 2 to 30 wt.-% and particularly preferably 5 to 20 wt.-% acidic radically polymerizable monomer(s),
- (b) 1 to 80 wt.-%, preferably 1 to 60 wt.-% and particularly preferably 5 to 55 wt.-% non-acidic radically polymerizable monomer(s),
- (c) 0 to 70 wt.-%, preferably 5 to 60 wt.-% and particularly preferably 10 to 50 wt.-% solvent(s),
- (d) 0 to 70 wt.-%, preferably 5 to 60 wt.-% and particularly preferably 8 to 50 wt.-% water, and optionally
- (e) 0 to 20 wt.-%, preferably 1 to 15 wt.-% filler(s), and optionally
- (f) 0.001 to 0.35 wt.-%, preferably 0.03 to 0.30 wt.-% and particularly preferably 0.05 to 0.25 wt.-% stabilizer(s).

The thixotropic agents optionally used to set the viscosity and the rheological properties are included in the quantity of filler.

According to an optional embodiment, the adhesive can moreover contain
- (g) 0.01 to 10 wt.-%, preferably 0.1 to 5.0 wt.-% and particularly preferably 0.5 to 4.5 wt.-% photoinitiator(s), and/or
- (h) 0.1 to 8 wt.-%, particularly preferably 0.2 to 7 wt.-% and quite particularly preferably 3 to 6 wt.-% thickener and/or
  6 to 12 mmol KOH per 100 g adhesive.

The adhesive particularly preferably has the following composition:
- (a) 1 to 30 wt.-%, preferably 2 to 30 wt.-% and particularly preferably 5 to 20 wt.-% acidic radically polymerizable monomer(s),
- (b) 1 to 80 wt.-%, preferably 1 to 60 wt.-% and particularly preferably 5 to 55 wt.-% non-acidic radically polymerizable monomer(s), (c) 0 to 70 wt.-%, preferably 5 to 60 wt.-% and particularly preferably 10 to 50 wt.-% solvent(s), preferably methanol or ethanol,
(d) 0 to 70 wt.-%, preferably 5 to 60 wt.-% and particularly preferably 8 to 50 wt.-% water, and optionally
(e) 0 to 20 wt.-% filler.

Moreover, the adhesive can optionally contain
(f) 0.001 to 0.35 wt.-%, preferably 0.03 to 0.30 wt.-% and particularly preferably 0.05-0.25 wt.-% stabilizer(s) and/or
(g) 0.01 to 10 wt.-%, preferably 0.1 to 4.5 wt.-% and particularly preferably 0.5 to 4.0 wt.-% photoinitiator(s) and/or
(h) 0.1 to 8 wt.-%, particularly preferably 0.2 to 7 wt.-% and quite particularly preferably 3 to 6 wt.-% thickener.

The adhesive quite particularly preferably has the following composition:
(a) 10 to 20 wt.-% acidic radically polymerizable monomer(s), preferably 10-methacryloyloxydecyl dihydrogen phosphate,
(b) 30 to 55 wt.-% non-acidic radically polymerizable monomer(s), preferably 18 to 25 wt.-% monofunctional monomer, in particular HEMA, and 24 to 35 wt.-% difunctional monomer, in particular bis-GMA, 1,10-decanediol dimethacrylate, V-818 or a mixture thereof,
(c) 10 to 15 wt.-% solvent(s), preferably ethanol,
(d) 8 to 15 wt.-% water,
(e) 3 to 6 wt.-% filler, preferably fumed silica,
(f) 0.1 to 0.25 wt.-% stabilizer(s),
(g) 1.0 to 4.0 wt.-% photoinitiator(s),
(h) 3 to 6 wt.-% thickener, preferably methacrylate-modified polyacrylic acid with a weight-average molar mass of from 5,000 to 50,000 g/mol, and 6 to 12 mmol KOH per 100 g adhesive.

Unless otherwise indicated, all quantities are relative to the total mass of the adhesive. The individual quantity ranges can be chosen separately. The quantities for the photoinitiator include all initiator constituents, such as e.g. reducing agent.

Those adhesives which consist of the named substances are particularly preferred. Furthermore, those adhesives in which the individual substances are in each case selected from the above-named preferred and particularly preferred substances are preferred.

The adhesive is preferably stored in a multi-dose container, or particularly preferably a single-dose container.

A multi-dose container, such as e.g. a dropper bottle, contains a quantity of adhesive that is sufficient for several applications, and it is combined with one or more separate applicators, wherein the applicator is coated with a quantity of vanadium(IV) salt and optionally sulfinic and/or ascorbic acid that is sufficient for several applications, preferably for one application. When a multi-dose container is used, the required quantity of the adhesive is e.g. dropped into a spot plate. The number of drops is measured such that the ratio of adhesive to applicator coating lies in the desired range, i.e. a good curing and adhesive action are achieved. The adhesive is taken up from the spot plate with the coated applicator and rubbed into the tooth surface to be treated.

Alternatively, the adhesive can be stored in a multi-dose container, from which a pre-set quantity of the adhesive can be removed by means of a dosing device, such as e.g. a pen applicator. The removal is preferably effected via a replaceable cannula which is connected to the container and which is coated in the described manner. The cannula is preferably coated with a quantity of vanadium salt and optionally sulfinic acid or sulfinic acid derivative such as is necessary for curing the pre-set quantity of adhesive. The cannula is preferably at least partially flocked or provided with a sponge, bristles or rubber lamellae. One cannula can be used for several applications. However, a new cannula is preferably used to remove a further portion. Pen applicators suitable according to the invention are described in US 2009/0060624 A1 and are commercially available under the name VivaPen® from Ivoclar Vivadent AG. 3 to 15 mg of the adhesive are preferably dispensed per application. The pen applicator preferably contains approx. 2 ml of the adhesive.

A dental adhesive set in which the adhesive and the applicator are stored spatially separated in a single-dose container is preferred according to the invention, wherein the quantity of the adhesive in the container is matched to the quantity of vanadium(IV) salt and optionally sulfinic and/or ascorbic acid on the coated applicator such that, after being mixed with the applicator, the adhesive contains a quantity of vanadium(IV) salt and optionally sulfinic acid derivative that is sufficient for the radical curing. Through the pre-dosed portions of adhesive and vanadium salt, which only need to be mixed by the user, unsuitable mixing ratios and application errors are avoided and a high degree of application safety is guaranteed. Bottles with an adhesive reservoir which can additionally hold the coated applicator such that the components do not come into contact with each other accidentally are suitable e.g. as single-dose containers.

An example of a container is shown in FIG. 1. The container 1 comprises the upper part 2 and the housing 3. The upper part 2 contains the applicator 6 with the handle part 6a and the working end 6b. The housing 3 has a reservoir 4, which contains a pre-portioned quantity of the adhesive 5. The housing is protected against the penetration of foreign substances and the volatilization of contents by suitable measures, e.g. by a membrane or a sealing device. The combination of single-dose container and applicator is also called an application device. The application device is activated by introducing the applicator into the reservoir with the adhesive, for example by piercing a membrane (not shown) or overcoming a sealing device (not shown) when the applicator is pressed down. Preferred application devices are described in EP 1 103 230 A2 and EP 1 459 697 A2 and corresponding U.S. Pat. No. 6,857,805, which US patent is hereby incorporated by reference.

The quantity of vanadyl(IV) salt and optionally sulfinic acid applied to an applicator is sufficient to cure approximately 200 mg of the adhesive. The quantity of adhesive is preferably calculated such that, in the adhesive, a vanadyl (IV) salt concentration of from 0.04 to 2 wt.-%, particularly preferably 0.05 to 1.3 wt.-% and optionally a sulfinic acid concentration of from 0.08 to 4 wt.-%, particularly preferably 0.1 to 2.6 wt.-%, is achieved, in each case relative to the quantity of adhesive.

Single-dose containers which contain 90 to 110 mg adhesive are preferred according to the invention. These are preferably combined with an applicator, which is coated with 50 to 80 µg vanadyl(IV) salt. When the vanadium salt is completely dissolved, a vanadium salt concentration of from 0.045 to 0.09 wt.-% is achieved in the adhesive. In the case of multi-dose containers, a predefined quantity of adhesive is mixed and taken up with an applicator. Approximately 30 mg adhesive is preferably provided and taken up with the applicator, with the result that an applicator coated with 50 to 80 µg vanadium salt can be used to apply several portions of the adhesive. In the case of pen applicators, 3 to 15 mg adhesive is typically removed per application, with the result that here too an applicator, for example a cannula, coated with 50 μg vanadium salt is suitable for several applications.

The applicator coated according to the invention makes it possible to provide an adhesive in a storage-stable form. Vanadium salts and sulfinates dissolved in methacrylates already lead to radical formation and premature polymerization of the adhesive in the presence of oxygen, which diffuses from the air into the adhesive. According to the invention, a premature curing of the adhesive is prevented by the separation of vanadium(IV) salt and adhesive. Only immediately before the application of the adhesive is the applicator brought into contact with the adhesive, whereby the coating detaches from the applicator and disperses in the adhesive. In this way, the destabilizing radical formation with atmospheric oxygen is avoided, and a freshly produced adhesive mixture, which copolymerizes reliably with peroxidically or hydroperoxidically initiated composites, is available for each application.

The adhesives according to the invention are suitable for use with peroxidically and hydroperoxidically initiated composites, i.e. composite materials which contain a hydroperoxide or a peroxide as initiator for the radical polymerization. Even without prior light curing they copolymerize well with the composites and yield a strong bond strength. However, they can also be used together with light-curing composites, which are commonly used e.g. in direct restoration treatment. In this case, the adhesives preferably contain a photoinitiator.

The adhesive set according to the invention preferably also contains a composite material which contains a peroxide or preferably a hydroperoxide as initiator for the radical polymerization. By composites is meant dental materials which contain at least one radically polymerizable monomer, preferably at least one (meth)acrylate, and at least one filler. Composites which, in addition to at least one hydroperoxide, contain at least one thiourea derivative are particularly preferred.

Hydroperoxides preferred according to the invention are compounds of the formula R—(OOH)$_n$, in which R is an aliphatic or aromatic hydrocarbon radical and n is 1 or 2. Preferred radicals R are alkyl and aryl groups. The alkyl groups can be straight-chain, branched or cyclic. Cyclic alkyl radicals can be substituted by aliphatic alkyl groups. Alkyl groups with 4 to 10 carbon atoms are preferred. Aryl groups can be unsubstituted or substituted by alkyl groups. Preferred aromatic hydrocarbon radicals are benzene radicals which are substituted with 1 or 2 alkyl groups. The aromatic hydrocarbon radicals preferably contain 6 to 12 carbon atoms. Particularly preferred hydroperoxides are t-amyl hydroperoxide, 1,1,3,3-tetramethylbutyl hydroperoxide, t-butyl hydroperoxide, t-hexyl hydroperoxide, 2,5-dimethyl-2,5-di(hydroperoxy)hexane, diisopropylbenzene monohydroperoxide, paramenthane hydroperoxide, p-isopropylcumene hydroperoxide and mixtures thereof. Cumene hydroperoxide (CHP) is quite particularly preferred.

Preferred thiourea derivatives are the compounds listed in EP 1 754 465 A1 in paragraph [0009]. Particularly preferred thiourea derivatives are acetyl, allyl, pyridyl and phenyl thiourea, hexanoyl thiourea and mixtures thereof. Acetyl thiourea (ATU) and hexanoyl thiourea are quite particularly preferred.

Thiourea derivatives with the formula

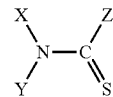

in which
X is H or Y,
Y is an alkyl radical with 1 to 8 carbon atoms, a cycloalkyl radical with 5 or 6 carbon atoms, a chlorine-, hydroxy- or mercapto-substituted alkyl radical with 1 to 8 carbon atoms, an alkenyl radical with 3 to 4 carbon atoms, an aryl radical with 6 to 8 carbon atoms, a chlorine-, hydroxy-, methoxy- or sulfonyl-substituted phenyl radical, an acyl radical with 2 to 8 carbon atoms, a chlorine- or methoxy-substituted acyl radical, an aralkyl radical with 7 to 8 carbon atoms or a chlorine- or methoxy-substituted aralkyl radical, and
Z is $NH_2$, NHX or $NX_2$
are further preferred.

In addition, the composites can also contain a transition metal compound, which is preferably selected from the compounds of the elements copper, iron, cobalt, nickel and manganese. Transition metal compounds of the metals copper, in particular $Cu^+$, iron, in particular $Fe^{3+}$, cobalt, in particular $Co^{3+}$, and nickel, in particular $Ni^{2+}$, are preferred. The transition metals are preferably used in the form of their salts. Preferred salts are the nitrates, acetates, 2-ethylhexanoates and halides, wherein chlorides are particularly preferred.

The transition metals can also be used in complexed form, wherein complexes with chelate-forming ligands are preferred. Preferred simple ligands are 2-ethylhexanoate and THF. Preferred chelate-forming ligands are 2-(2-aminoethylamino)ethanol, aliphatic amines, particularly preferably 1,1,4,7,10,10-hexamethyltriethylenetetramine (HMTETA), N,N,N',N'',N''-pentamethyldiethylenetriamine (PMDETA), tris[2-(dimethylamino)ethyl]amine (Me$_6$TREN), N,N,N',N'-tetramethylethylenediamine (TMEDA), 1,4,8,11-tetraaza-1,4,8,11-tetramethylcyclotetradecane (Me4CYCLAM), diethylenetriamine (DETA), triethylenetetramine (TETA) and 1,4,8,11-tetraazacyclotetradecane (CYCLAM); pyridine-containing ligands, particularly preferably N,N,N',N'-tetrakis(2-pyridylmethyl)ethylenediamine (TPEN), N,N-bis(2-pyridylmethyl)amine (BPMA), N,N-bis(2-pyridylmethyl) octylamine (BPMOA), 2,2'-bipyridine and 8-hydroxyquinoline. Quite particularly preferred ligands are acetylacetone, dimethylglyoxime and 1,10-phenanthroline.

In the case of electrically neutral ligands, the charge of the transition metal ions must be balanced by suitable counterions. In particular, the above-named ions which are used to form salts are suitable for this purpose, with acetates and chlorides being particularly preferred. Chlorides and complexes are characterized by a relatively good solubility in the monomers which are used to produce the dental materials.

Instead of the transition metal complexes, non-complex salts of the transition metals in combination with complex-forming organic compounds can be used to produce the dental materials. The organic ligands form the catalytically active complexes when mixed with the transition metal salts.

Preferred copper salts are Cu(II) carboxylates (e.g. of acetic acid or 2-ethylhexanoic acid), $CuCl_2$, $CuBr_2$, $CuI_2$, particularly preferably CuBr and quite particularly preferably CuCl. Preferred copper complexes are complexes with the ligands acetylacetone, phenanthroline (e.g. 1,10- phenanthroline (phen)), aliphatic amines, such as e.g. 1,1,4,7,10,10-hexamethyltriethylenetetramine (HMTETA), N,N,N',N'',N''-pentamethyldiethylenetriamine (PMDETA), tris[2-(dimethylamino)ethyl]amine (Me$_6$TREN).

Preferred iron salts are FeCl$_3$, FeBr$_2$ and FeCl$_2$. Preferred iron complexes are complexes with the ligands acetylacetone, triphenylphosphine, 4,4'-di(5-nonyl)-2,2'-bipyridine (dNbpy) or 1,3-diisopropyl-4,5-dimethylimidazol-2-ylidene (Prilm). The complexes Fe(acac)$_2$ and FeCl$_2$(PPh$_3$)$_2$ are quite particularly preferred.

Preferred nickel salts are NiBr$_2$ and NiCl$_2$, preferred nickel complexes are nickel acetylacetonate and NiBr$_2$(PPh$_3$)$_2$.

According to the invention, copper compounds, copper complexes and in particular mixtures of copper salts and complexing organic ligands are preferred, particularly salts and complexes of the monovalent copper (Cu$^+$), such as e.g. copper(I) chloride (CuCl). Compositions which contain a salt of monovalent copper are characterized by a good storage stability.

Composites which contain
(a) 0.001 to 5.0 wt.-%, preferably 0.005 to 3.0 wt.-%, particularly preferably 0.1 to 3.0 wt.-% at least one thiourea derivative,
(b) 0.01 to 5.0 wt.-%, preferably 0.05 to 4.0 wt.-% and particularly preferably 0.1 to 3.0 wt.-% at least one hydroperoxide,
(c) 5 to 95 wt.-%, preferably 10 to 95 wt.-% and particularly preferably 10 to 90 wt.-% at least one radically polymerizable monomer,
(d) 0 to 80 wt.-% filler(s), and
(e) 0.01 to 5 wt.-%, preferably 0.1 to 3 wt.-% and particularly preferably 0.1 to 2 wt.-% additive(s) and optionally
(f) 0.0001 to 1 wt.-%, preferably 0.0005 to 0.5 wt.-%, particularly preferably 0.0007 to 0.02 wt.-% at least one transition metal compound
are preferred according to the invention.

Unless otherwise indicated, all quantities here are relative to the total mass of the composition. The components named above as constituents of the adhesive are preferred as monomers, fillers and adhesives.

The filling level is geared towards the desired intended use of the material. Preferably filling composites have a filler content of from 50 to 80 wt.-%, particularly preferably 70 to 80 wt.-%, and dental cements have a filler content of from 10 to 70 wt.-%, particularly preferably 60 to 70 wt.-%. Prosthesis materials preferably have a filler content of from 0 to 10 wt.-%, particularly preferably 0 to 5 wt.-%.

The adhesive sets according to the invention are suitable primarily for intraoral application by the dentist for the restoration of damaged teeth, i.e. for therapeutic use. They are particularly suitable for indirect restoration treatment, e.g. as adhesive cements or as adhesives for cementing dental restorations made of ceramic, glass ceramic, metal or cured composites to the tooth. However, they are also suitable for application together with filling composites for direct restoration treatment. Furthermore, they can be used extraorally (non-therapeutically), for example in the production or repair of dental restorations, such as inlays, onlays, crowns and bridges.

The invention is explained in more detail below with reference to figures and embodiment examples.

FIG. 1 shows a two-part single-dose container 1 with an upper part 2 and a lower housing 3. The housing has a reservoir 4 for the adhesive 5. The upper part contains a coated applicator 6. The upper part 2 shown in FIG. 1 has holes at 7, through which the adhesive 5 can penetrate into the upper part when the upper part 2 is dipped into the adhesive.

Figure 2:
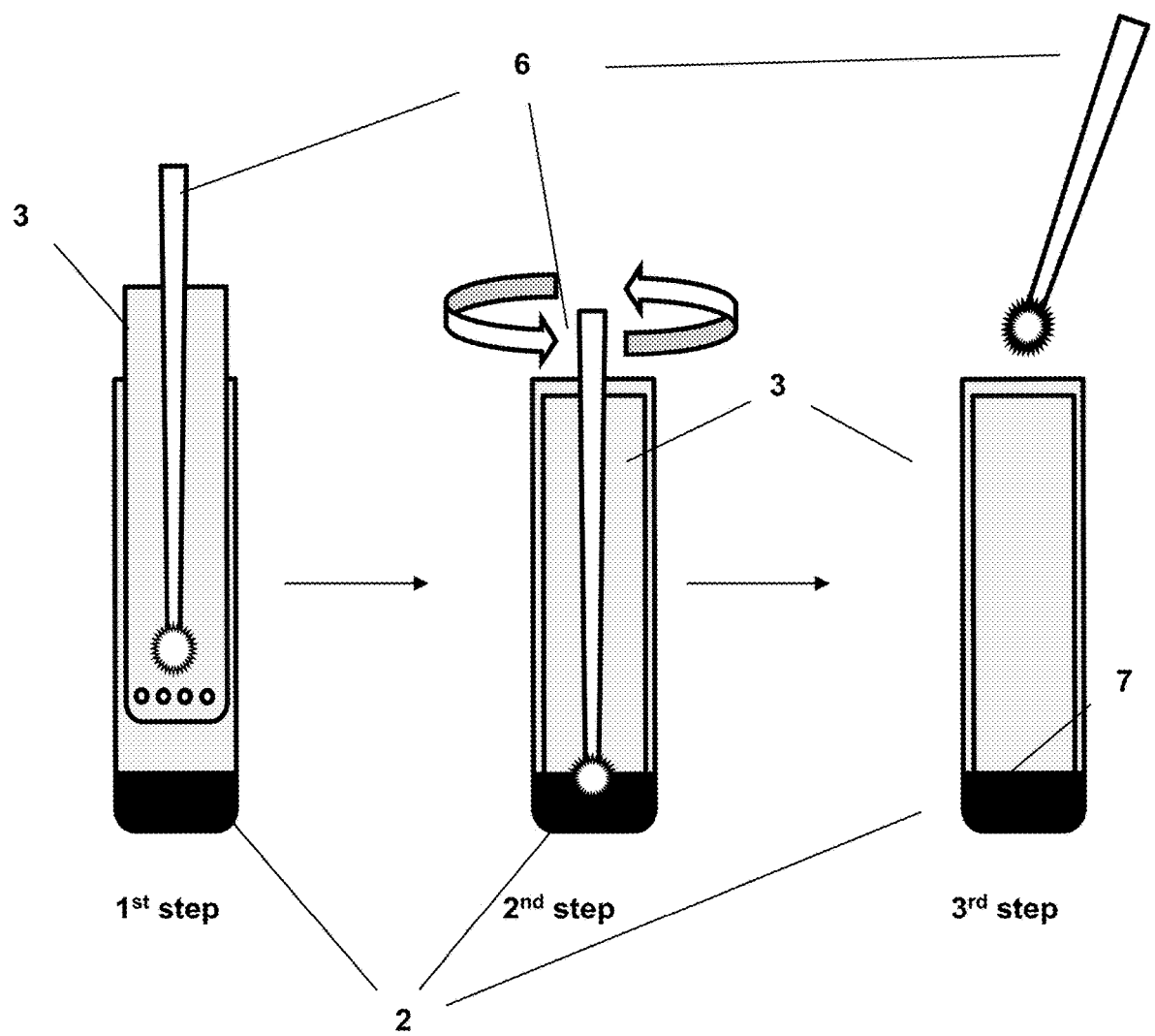
FIG. 2 shows the use of the adhesive in accordance with the invention.

FIG. 2 illustrates the use of the adhesive according to the invention. Before use, the lower half 2 and the upper half 3 of the container are pushed together, and thus the applicator 6 is brought into contact with the adhesive 5 (1$^{st}$ step). In the second step, the applicator 6 is moved in the adhesive 5 and thus the ready-to-use adhesive 7 is formed. In the third step, this can be applied e.g. to a tooth surface with the applicator 6.

EXAMPLES

Examples 1 to 7

Production of Coated Applicators and Measurement of the Adhesion

To produce coated applicators, the tip of small brushes (Microbrush Tube Series, manufacturer: Microbrush) was dipped into the solutions listed in Table 1 in the specified sequence. After each dipping step, the brushes were dried for 5 to 10 minutes at 40° C. in a drying cabinet. Then the brushes were dipped into an adhesive with the composition specified in Table 2 (approx. 90-110 mg), the adhesive was stirred for approx. 3-5 seconds with the brush and then applied to tooth surfaces, rubbed in on the tooth surface for 20 s with the brush (contact pressure sufficient to slightly deform the brush shaft) and dried with an airstream (4 bar, oil-free) from an air-spraying unit for approx. 5 seconds. The adhesive layer was not cured before the composite was deposited.

A two-component, self-curing peroxide- or hydroperoxide-containing composite was then applied to the tooth surfaces coated with adhesive. The adhesion values were determined on bovine dentine according to ISO 29022. The sample preparation and test specimen dimensions were in accordance with ISO 29022. Prepolymerized cylinders made of a pressure-stable dental composite (Tetric EvoCeram, height approx. 1.5 mm, diameter approx. 2.37 mm) were produced, roughened on an end face with a sandblaster (Renfert Basic Quattro, 100 μm aluminium oxide, 1 bar) and applied to the tooth surface pretreated with adhesive with the luting composite to be tested. A 500-g weight guided perpendicularly ensured that the tooth surface and the longitudinal axis of the cylinder were arranged orthogonal to each other. The contact pressure along the longitudinal axis of the cylinder was maintained for 15 minutes under exclusion of light at room temperature. The composite cured completely in this time. Then, the test piece was stored in water for 24 h at 37° C. and loaded to failure as described in ISO 29022. The determination of the bond strength was effected according to ISO 29022 with a universal testing machine of the ZWICK-ROELL 010 type. The adhesion values measured are listed in Table 1.

To determine the storage stability, the coated applicators and the adhesive were stored at 50° C. for 2 and also 8 weeks. At regular intervals, samples were taken and the adhesion was determined on bovine dentine, as described above. The values for the hydroperoxide-containing composite are given in Table 1.

Examples 1 to 7 show the adhesion values which were achieved with brushes coated according to the invention. Both peroxide-containing and hydroperoxide-containing composite achieved good adhesion values. Examples 1 and 2 show the adhesion values for brushes which were coated first with the vanadium salt and then with a sulfinic acid compound. In these examples, much better adhesion values were measured with the peroxidic composite than in the case of the reverse coating sequence (Examples 3 and 4) or in the case of application of vanadium compound and sulfinate together (Examples 5 and 6). An adhesion of over 9 MPa was achieved on enamel and dentine, which is more than sufficient for clinical use. The adhesives are characterized by a good storage stability of 2 and 8 weeks at 50° C., respectively. Example 7 shows that, even without sulfinate, vanadium(IV) oxalate yields excellent adhesion values both with peroxide-containing and with hydroperoxide-containing composites.

TABLE 1

Production of coated applicators and adhesion values

| | | | Dentine adhesion values | | | |
|---|---|---|---|---|---|---|
| | | | Peroxide-containing | Hydroperoxide-containing composite[2]) | | |
| Ex. | Dipping step 1 | Dipping step 2 | composite[1]) After production | After production | After 2 weeks @ 50° C. | After 8 weeks @ 50° C. |
| 1 | Vanadyl acetylacetonate/ascorbic acid[3]) | Sodium benzenesulfinate[4]) | 13.5 ± 4.1 MPa | 32.6 ± 5.9 MPa | 18.2 ± 4.1 MPa | Not determined |
| 2 | Vanadyl picolinate/ascorbic acid[5]) | Sodium benzenesulfinate[4]) | 10.2 ± 4.4 MPa | 29.2 ± 3.1 MPa | 19.3 ± 3.9 MPa | Not determined |
| 3 | Sodium benzenesulfinate[4]) | Vanadyl acetylacetonate/ascorbic acid[3]) | 3.9 ± 3.6 MPa | 28.8 ± 1.8 MPa | Not determined | Not determined |
| 4 | Sodium benzenesulfinate[4]) | Vanadyl picolinate/ascorbic acid[5]) | 4.2 ± 2.2 MPa | 30.1 ± 2.7 MPa | Not determined | Not determined |
| 5 | Vanadyl acetylacetonate/ascorbic acid/sodium benzenesulfinate[6]) | — | 4.1 ± 2.8 MPa | 32.4 ± 1.6 MPa | Not determined | Not determined |
| 6 | Vanadyl picolinate/ascorbic acid/sodium benzenesulfinate[7]) | — | 3.6 ± 4.2 MPa | 30.1 ± 2.0 MPa | Not determined | Not determined |
| 7 | Vanadyl oxalate[8]) | — | 9.0 ± 1.1 MPa | 31.4 ± 3.3 MPa | 26.2 ± 3.0 MPa | 23.5 ± 6.7 MPa |

[1])Self-curing peroxide-containing composite (Multicore Flow; Ivoclar Vivadent AG)
[2])Self-curing hydroperoxide-containing composite (Variolink Esthetic DC; Ivoclar Vivadent AG)
[3])Solution of 2 wt.-% vanadyl acetylacetonate and 1 wt.-% ascorbic acid in methanol
[4])Solution of 2 wt.-% sodium benzenesulfinate in ethanol
[5])Solution of 2 wt.-% vanadyl picolinate and 1 wt.-% ascorbic acid in methanol
[6])Solution of 2 wt.-% vanadyl acetylacetonate, 1 wt.-% ascorbic acid and 2 wt.-% sodium benzenesulfinate in methanol
[7])Solution of 2 wt.-% vanadyl picolinate, 1 wt.-% ascorbic acid and 2 wt.-% sodium benzenesulfinate in methanol
[8])Solution of 1 wt.-% vanadyl oxalate in methanol

TABLE 2

Composition of the adhesive

| Constituent | wt.-% | Name |
|---|---|---|
| a | 12.50% | MDP[4]) - phosphate methacrylates |
| | 4.33% | PO-25[11]) - polyacrylic acid methacrylate |
| b | 19.68% | HEMA[1]) - monofunctional monomer |
| | 19.23% | Bis-GMA[2]) - crosslinker |
| | 8.65% | D3MA[3]) - crosslinker |
| c | 12.50% | Ethyl alcohol |
| d | 11.57% | $H_2O$ |
| e | 3.85% | Aerosil 200[5]) |
| f | 0.17% | BHT[6]) - stabilizer |
| | 0.01% | MEHQ[7]) - stabilizer |
| | 0.01% | TEMPO[12]) - stabilizer |
| | 3.85% | Potassium hydroxide 2M in water |
| g | 0.96% | Chivacure EPD[8]) - amine |
| | 1.73% | Camphorquinone[9]) (photoinitiator) |
| | 0.96% | DMAEMA[10]) - amino methacrylate |
| Total | 100.00% | |

[1])2-hydroxyethyl methacrylate, CAS No. 868-77-9
[2])bisphenol A glycerolate dimethacrylate, CAS No. 1565-94-2
[3])1,10-decanediol dimethacrylate, CAS No. 6701-13-9
[4])10-methacryloyloxydecyl dihydrogen phosphate, CAS No. 85590-00-7
[5])fumed silica with a specific surface area (BET) of 200 m²/g (CAS No. 112 945-53-5; EVONIK)
[6])2,6-di-tert-butyl-4-methylphenol, CAS No. 204-881-4
[7])4-methoxyphenol, CAS No. 150-76-5
[8])ethyl p-(dimethylamino)benzoate, CAS No. 10287-53-3
[9])camphorquinone, CAS No. 10373-78-1
[10])2-(dimethylamino)ethyl methacrylate, CAS No. 2867-47-2
[11])glycidyl methacrylate-modified polyacrylic acid, CAS No. 54351-53-0
[12])2,2,6,6-tetramethylpiperidinooxyl (TEMPO), CAS No. 2564-83-2

The invention claimed is:

1. A dental adhesive set which comprises
an adhesive and
an applicator, which is coated with one or more vanadium (IV) salts but does not comprise an oxidizing agent and a composite material that comprises a hydroperoxide or a peroxide as initiator for the radical polymerization.

2. The dental adhesive set according to claim 1, in which the applicator is coated with vanadyl (IV) oxalate and/or vanadyl (IV) acetylacetonate and/or vanadyl (IV) picolinate.

3. The dental adhesive set according to claim 1, in which the applicator is additionally coated with at least one sulfinic acid and/or sulfinic acid derivative.

4. The dental adhesive set according to claim 1, in which the applicator is additionally coated with a reducing agent.

5. The dental adhesive set according to claim 1, in which the adhesive comprises
   (a) at least one radically polymerizable acidic monomer,
   (b) at least one radically polymerizable monomer without acidic groups,
   (c) at least one water-miscible organic solvent,
   (d) water, and
   (e) optionally one or more fillers, and
   (f) optionally one or more stabilizers, and
   (g) optionally a photoinitiator for the radical polymerization and
   (h) optionally a thickener.

6. The dental adhesive set according to claim 5, in which the adhesive comprises
   (a) 1 to 40 wt.-% of at least one radically polymerizable acidic monomer,
   (b) 1 to 80 wt.-% of at least one radically polymerizable monomer without acidic groups,
   (c) up to 70 wt.-% of at least one water-miscible organic solvent,
   (d) up to 70 wt.-% water, and
   (e) optionally 0 to 20 wt.-% of at least one filler, and
   (f) optionally 0.001-0.35 wt.-% of at least one stabilizer, and
   (g) optionally 0.01 to 10 wt.-% photoinitiator, and
   (h) optionally 0.1 to 8 wt.-% thickener,
   in each case relative to the total mass of the composition.

7. The dental adhesive set according to claim 1, in which the applicator is coated with vanadyl (IV) oxalate and the composite material comprises a hydroperoxide as initiator for the radical polymerization.

8. The dental adhesive set according to claim 1, in which the adhesive and the applicator are stored spatially separated in a single-dose container, wherein a quantity of the adhesive is matched to a quantity of the one or more vanadium (IV) salts and optionally a sulfinic acid, a sulfinic acid derivative, an ascorbic acid and/or an ascorbic acid derivative on the coated applicator such that, after being mixed with the applicator, the adhesive contains a quantity of the one or more vanadium (IV) salts and optionally a sulfinic acid, a sulfinic acid derivative, an ascorbic acid and/or an ascorbic acid derivative for performing radical curing.

9. The dental adhesive set according to claim 1, in which the applicator and the adhesive are stored spatially separated from each other in a multi-dose container, wherein a quantity of the one or more vanadium (IV) salts and optionally a sulfinic acid derivative on the coated applicator is measured such that, after a predefined quantity of the adhesive has been mixed with the applicator, the adhesive contains a quantity of the one or more vanadium (IV) salts and optionally the sulfinic acid derivative for performing radical curing.

10. The dental adhesive set according to claim 1 for therapeutic use in intraoral restoration of damaged teeth.

11. The dental adhesive set according to claim 3, in which the at least one sulfinic acid and/or sulfinic acid derivative comprises a sulfinic acid ester and/or sulfinic acid salt.

12. The dental adhesive set according to claim 4, in which the reducing agent comprises ascorbic acid or an ascorbic acid derivative.

13. The dental adhesive set according to claim 5, in which the adhesive comprises
   (a) 2 to 30 wt.-% of at least one radically polymerizable acidic monomer,
   (b) 1 to 60 wt.-% of at least one radically polymerizable monomer without acidic groups,
   (c) 5 to 60 wt.-% of at least one water-miscible organic solvent,
   (d) 5 to 60 wt.-% water, and
   (e) optionally 0 to 20 wt.-% of at least one filler and
   (f) optionally 0.03 to 0.30 wt.-% of at least one stabilizer, and
   (g) optionally 0.1 to 4.5 wt.-% of a photoinitiator, and
   (h) optionally 0.2 to 7 wt.-% thickener,
   in each case relative to the total mass of the composition.

14. The dental adhesive set according to claim 5, in which the adhesive comprises
   (a) 5 to 20 wt.-% of at least one radically polymerizable acidic monomer,
   (b) 5 to 55 wt.-% of at least one radically polymerizable monomer without acidic groups,
   (c) 10 to 50 wt.-% of at least one water-miscible organic solvent,
   (d) 8 to 50 wt.-% water, and
   (e) optionally 0 to 20 wt.-% of one or more fillers, and
   (f) optionally 0.05 to 0.25 wt.-% of at least one stabilizer, and
   (g) optionally 0.5 to 4.0 wt.-% photoinitiator, and
   (h) optionally 3 to 6 wt.-% thickener,
   in each case relative to the total mass of the composition.

15. The dental adhesive set according to claim 11, in which the at least one sulfinic acid and/or sulfinic acid derivative comprises sodium benzenesulfinate and/or lithium benzenesulfinate.

* * * * *